United States Patent
Andersen

[19]

[11] Patent Number: 5,833,275
[45] Date of Patent: Nov. 10, 1998

[54] LOCKING MEDICAL CONNECTOR

[75] Inventor: Erik Andersen, Gurnee, Ill.

[73] Assignee: Corpak, Inc., Wheeling, Ill.

[21] Appl. No.: 346,471

[22] Filed: Nov. 29, 1994

[51] Int. Cl.⁶ ........................................ F16L 37/08
[52] U.S. Cl. ...................... 285/305; 265/307; 265/317
[58] Field of Search ........................... 285/314, 360, 285/305, 307, 317

[56]  References Cited

U.S. PATENT DOCUMENTS

| | | | |
|---|---|---|---|
| 921,368 | 5/1909 | Crook | 285/314 X |
| 1,074,706 | 10/1913 | Ferguson | 285/360 |
| 2,103,050 | 12/1937 | White | 285/360 X |
| 2,755,107 | 7/1956 | Dow | 285/317 X |
| 2,941,822 | 6/1960 | Moecka | 285/314 X |
| 3,272,538 | 9/1966 | Bergstrom | 285/317 X |
| 3,645,562 | 2/1972 | Fandetti et al. | 285/360 X |
| 3,722,927 | 3/1973 | Miska | 285/317 |
| 4,076,285 | 2/1978 | Martinez . | |
| 4,296,949 | 10/1981 | Muetterties et al. . | |
| 4,323,065 | 4/1982 | Kling . | |
| 4,346,703 | 8/1982 | Dennehey et al. . | |
| 4,439,188 | 3/1984 | Dennehey et al. . | |
| 4,576,359 | 3/1986 | Oetiker | 285/317 X |
| 4,588,402 | 5/1986 | Igari et al. . | |
| 4,607,868 | 8/1986 | Harvey et al. . | |
| 4,639,019 | 1/1987 | Mittleman . | |
| 4,820,288 | 4/1989 | Isono . | |
| 4,929,236 | 5/1990 | Sampson . | |
| 4,963,133 | 10/1990 | Whipple . | |
| 4,969,879 | 11/1990 | Lichte . | |
| 4,991,629 | 2/1991 | Ernesto et al. . | |
| 5,047,021 | 9/1991 | Utterberg . | |
| 5,049,139 | 9/1991 | Gilchrist . | |
| 5,104,157 | 4/1992 | Bahna | 285/314 X |
| 5,143,347 | 9/1992 | Lee et al. | 285/317 X |
| 5,316,041 | 5/1994 | Ramalier | 285/317 X |

FOREIGN PATENT DOCUMENTS 2556878  6/1977  Germany ......................... 285/314

*Primary Examiner*—Dave W. Arola
*Attorney, Agent, or Firm*—Wallenstein & Wagner, Ltd.

[57]  ABSTRACT

An apparatus for connecting tubing which comprises a connector body having an inner lumen and an outer surface, a connector sleeve having an inner surface which defines a passageway, at least a portion of the connector body insertable into the connector sleeve and the surfaces thereof in slidable engagement, a shoulder and a latch on the surfaces in slidable engagement, and the latch positioned to engage with the shoulder to lock the connector body inserted within the connector sleeve.

7 Claims, 2 Drawing Sheets

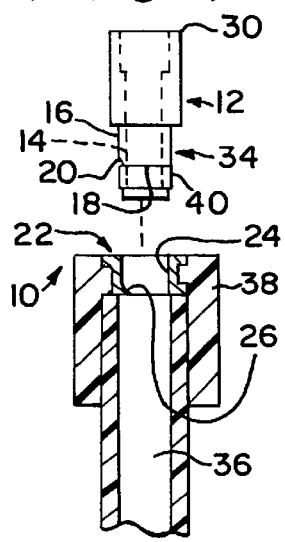
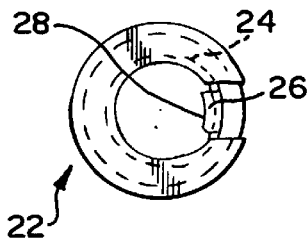
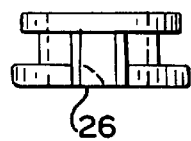
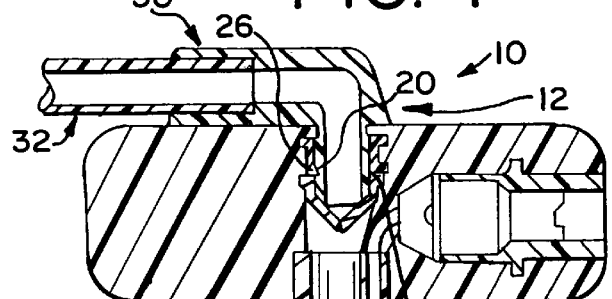
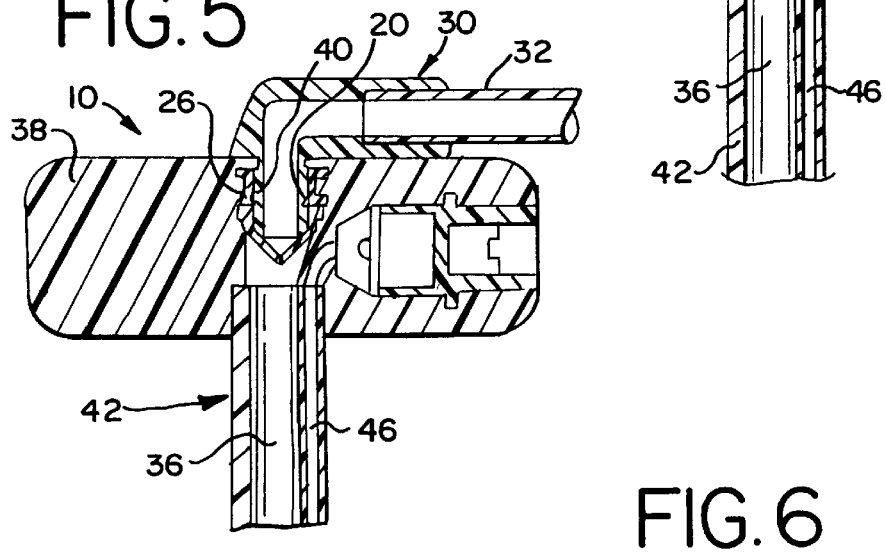
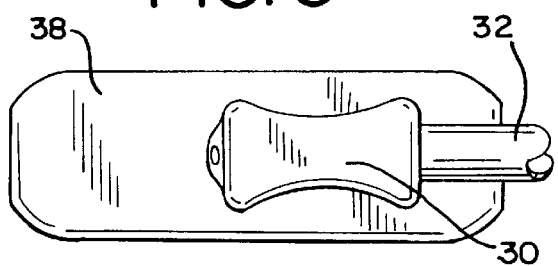

LOCKING MEDICAL CONNECTOR

TECHNICAL FIELD

The present invention relates to a medical connector, and in particular to a device for connecting medical tubing, such as for connecting a tubing of a percutaneous access device.

BACKGROUND OF THE INVENTION

During the medical treatment of some patients, it is necessary for a patient to undergo therapy which involves administration or removal of fluids. Such medical procedures are typically used to assess internal functions, detect medical complications, treat medical problems, administer medications or nutrients, and to decompress or re-inflate the stomach and duodenum. The medical procedures usually involve administration of fluid preparations or removal of fluids through a flexible tubing, often of relatively small diameter. The tubing is administered either nasally or orally, or through a surgically formed stoma for percutaneous access. Subsequent to the medical tubing being inserted or implanted in the patient, the medical tubing is connected to the necessary tubing for the medical procedure being performed.

During the medical procedure, it is often imperative to maintain the connection of the medical tubing. Disconnection of the tubes during the medical procedure will likely cause a spill of the fluid, as well as potential physical harm to the patient due to the absence of administration of the medical preparation into the patient, and the potential for infection and emotional trauma. Therefore, there exists a need for a locking connection between the medical tubes during a medical procedure.

Further, it is often necessary for the fluid therapy to continue over an extended period of time, or in repeated intervals. Often, the medical device or tubing which is inserted or implanted in the patient is intended to remain in place, and has a proximal end located outside the patient for attachment of medical tubing. Therefore, it is often necessary to disconnect and re-connect the medical tubing. For example, some patients require enteral feeding, such as through percutaneous access. When a percutaneous gastrostomy device is used to administer nutrients to a patient, the gastrostomy tube is implanted in the patient and is secured in place, and the feeding tube from the nutrient source must be connected to the gastrostomy tube. Preferably, the gastrostomy tube remains implanted in the patient between feedings or when the nutrition source is expended or otherwise changed. It is necessary to temporarily and securely attach the gastrostomy tubing to an administrative set, i.e., a nutrient source tube. Therefore, there exists a need for a suitable connector between such medical tubes which permits secure connection, disconnection, and re-connection.

Also, the medical device used for fluid therapy typically has numerous tubes or ports for connecting tubes, each for performing separate functions associated with the specific medical procedure being performed. Often, tubes are connected to different tubes or ports which are in close proximity to one another, and are similar in appearance. It is important that such different tubes or ports are not mistaken for one another. Therefore, there exists a need for a tubing connector which minimizes or prevents the possibility that persons will be confused between the different tubes during a medical procedure.

For example, in the case of a gastrostomy tube, a gastrostomy device typically includes a feeding tube and other tubes, such as an inflation tube which is utilized to inflate a balloon-like retention member of the gastrostomy device. The proximal end of the feeding tube and that of the inflation tube often are in close proximity to one another. It is very important that the person connecting the nutrient source to the gastrostomy device does not confuse the inflation tube with the feeding tube. If such confusion of the tubing occurs, and the nutrient source is erroneously attached to the inflation tubing, the inflatable retention member of the gastrostomy device will likely fill up with nutrient and burst in the patient. The gastrostomy device must then be replaced, causing discomfort and additional expense to the patient, and increasing the possibility of infection and other medical complications.

Prior art means of connecting such medical tubing typically include either screw-type connectors, or connectors which are force-fitted into an opening which is subject to a certain degree of elastic deformation.

The screw-type connector typically includes a first and second half, each attached to the and of the tubes to be joined. The first half includes threading, and the second half includes comparable threading, or at least a rib, which is adapted to engage the threading of the first half and is rotatable to tighten the connection. This type of connector, however, requires that the tubing be rotated relative to the each other as the connector parts are joined. Such rotation of the tubing is likely to cause deformation or stress on the tubing, increasing the likelihood that the tube may rotate in reverse fashion, and the union may loosen or disconnect. Further, tugging or twisting action on the tubes may cause the union of a screw-type connector to be accidentally disconnected. Other problems associated with screw-type connectors, relating particularly with the type of connector known as the Luer adaptor, are discussed in U.S. Pat. No. 4,538,836 (Column 2, lines 12–55).

Another type of prior art connector of medical tubing utilizes a relatively rigid connector body which is force-fitted into the lumen of the tubing, subjecting the tubing to a certain degree of elastic deformation as the tubing is expanded to fit over the end of the connector. However, because the tubing is typically made of a semi-elastic material, such as silicone, the tubing is extremely slippery when wet. Therefore, this type of connection will usually fail when the tubing is wet prior to joining with the rigid connector. Also, because the elastic properties of the tubing will likely change when subjected to deformation over an extended period of time, the attachment of the tube to the rigid connector is likely to become loose, allowing disconnection or allowing fluid to seep between the tube and the rigid connector. Further, because this type of union is merely by force fitting the tube over a portion of the connector, the union will likely disconnect when the tubing is subjected to tugging or bending action.

Therefore, there exists a need for a suitable connector for medical tubing which addresses the problems discussed above.

SUMMARY OF THE INVENTION

It is the object of the present invention to provide a locking connection between medical tubing which includes a connector body that is received into a connector sleeve. The connector body is attached to a first tube, and the connector sleeve is attached to a second tube. The connecting surfaces of the body and the sleeve include a shoulder and a latch which engage together to form a locking union of the fluid passageway of the tubes.

Another aspect of the present invention is to provide a locking connection between medical tubing which may be unlocked. A passage through the shoulder provides for the latch to be disengaged from the shoulder, thereby unlocking the connector.

Other advantages and aspects of the present invention will become apparent upon reading the following description of the drawings and detailed description of the invention.

BRIEF DESCRIPTION OF THE DRAWING

FIG. 1 is a side cross-section view of one embodiment of the present invention;

FIG. 2 is a plan view of the circular connector sleeve portion of one embodiment of the present invention;

FIG. 3 is a side view of that shown in FIG. 2;

FIG. 4 is a cross-section view of an alternative embodiment of the present invention shown in a locked position;

FIG. 5 is the apparatus of FIG. 4 shown in an unlocked, or disengaged, position;

FIG. 6 is a plan view of the apparatus shown in FIG. 5;

DETAILED DESCRIPTION

Figure 7:
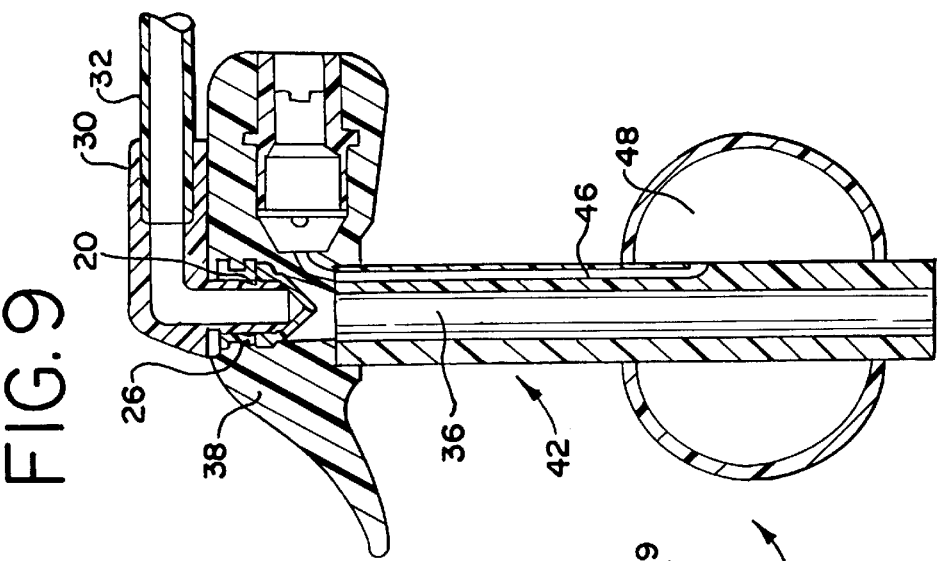
FIG. 7 is a disassembled perspective view of another embodiment of the present invention as it is used in a gastrostomy tube.
Figure 8:
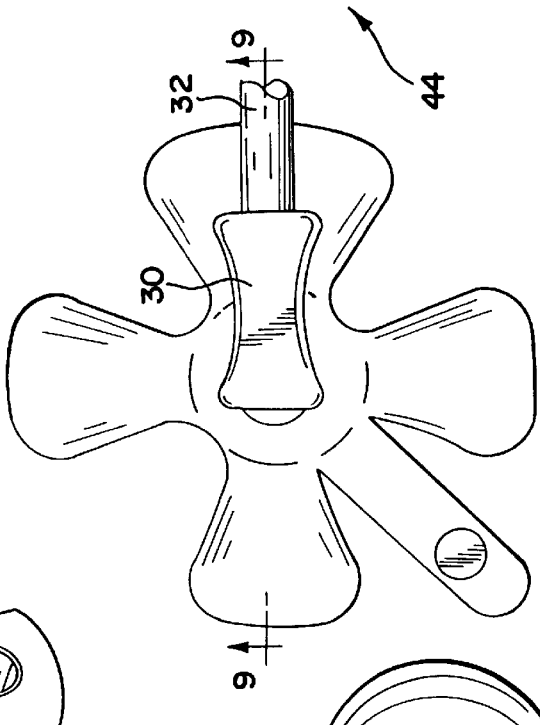
FIG. 8 is a top plan view of the apparatus shown in FIG. 7.

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiments illustrated.

As shown in FIG. 1, the locking connector 10 is comprised of a connector body 12 and a connector sleeve 22. The connector body 12 has a distal end 30 which is attached to a first tube 32 and a proximal end 34. The connector body 12 has an inner surface 14 and an outer surface 16. The inner surface 14 of the connector body 12 forms a passageway through the connector body.

The connector sleeve 22 of the locking connector 10 has an inner surface 24. The inner surface 24 defines a passageway through the connector sleeve 22, which is of slightly greater diameter than the outer surface 16 of the connector body 12, so that at least a portion of the proximal end of connector body 12 may be inserted within the connector sleeve 22. The connector sleeve 22 may be positioned within the lumen of a second tube 36, or, as shown in FIG. 1, may be aligned with the second tube and secured thereto by an outer coupling 38.

The connector body 12 and the connector sleeve 22 are joined together to permit fluid flow from one tube to the other, preferably from the first tube to the second tube.

The locking connector 10 includes a shoulder 18, preferably located on the outer surface 16 of the connector body 12. The embodiment of the invention shown in FIG. 1 discloses the shoulder 18 being defined by a recess 20 in the outer surface 16 of the connector body 12. However, the shoulder of the present invention also may be defined by a protrusion.

The locking connector 10 also includes a latch 26, preferably located on the inner surface 24 of connector sleeve 22, which engages with the shoulder 18 when the connector body 12 is joined with the connector sleeve 22. In the preferred embodiment, the proximal end of the connector body 12 is inserted into the connector sleeve 22, and the two are locked together as the latch 26 engages with the shoulder 18.

In the preferred embodiment, as is best shown in FIGS. 2 and 3, the latch 26 protrudes inwardly from the inner surface 24 of the connector sleeve 22 and terminates at a latch tip 28. The connector sleeve 22 and latch 26 are preferably formed of a semi-rigid material, such as plastic, which is somewhat pliable and permits movement of the latch 26 outwardly when subjected to force. It is also preferable for the material surrounding the connector sleeve be formed of a rubber-like material, such as silicone, which is subject to elastic deformation as the latch 26 is forced outwardly. Therefore, when the proximal end of the connector body 12 is inserted into the connector sleeve 22, the outer surface 16 of the connector body 12 applies force on the latch 26, forcing it outwardly such that the latch tip 28 is in general alignment with the inner surface 24 of the connector sleeve 22. In this manner, the connector body is inserted further into the connector ring until the latch tip 28 engages with the shoulder 18.

Once the connector body 12 and the connector sleeve 22 is locked together, these parts of the locking connector 10 may not be separated unless the latch 26 is disengaged from the shoulder 18. In the preferred embodiment, the shoulder 18 extends only partially around the circumference, thereby forming a passage 40. Once the latch 26 is aligned with the passage 40, the latch 26 is no longer engaged with the shoulder 18, and the connector body 12 may be separated from the connector sleeve 22.

FIGS. 4 through 9 show alternative embodiments of the present invention as a connector of tubing from a nutrient source to the feeding tube 42 of a gastrostomy device 44. As shown in FIG. 4, the connector body 12 is inserted into the connector sleeve 22, and the latch 26 engages with the shoulder 18. As shown in FIGS. 5 and 6, when the latch 26 is aligned with the passage 40, the latch 26 is no longer engaged with the shoulder 18, and the connector body 12 may be separated from the connector sleeve 22.

Figure 9:
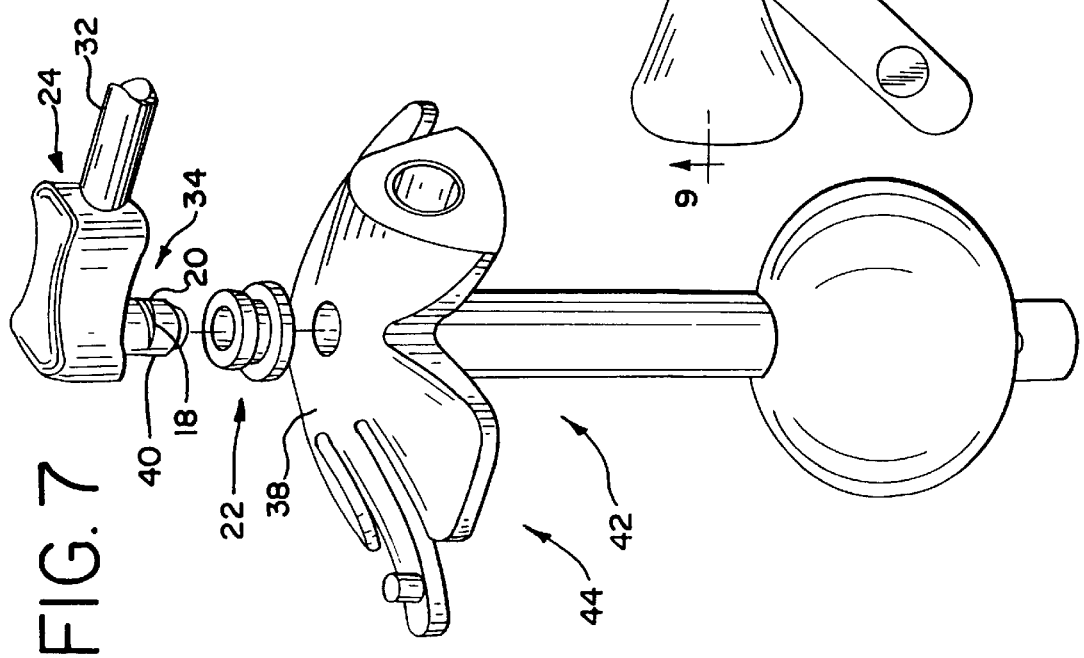
FIG. 9 is a cross-section side view of the apparatus shown in FIG. 7.

As is best shown in FIG. 9, a gastrostomy device 44 typically includes a feeding tube 42 and an inflation tube 46, used to inflate a retention member 48 inside the patient's stomach. The present invention includes a locking connector 10 which provides union of specific tubing (in this case, feeding tubing), thereby eliminating the potential for attaching tubing incorrectly, such as attachment of the nutrition source tube to the inflation tube 46.

Another feature of the embodiment which is shown in FIGS. 4 through 9 is that the distal end and proximal end of the connector body 12 are at approximate right angle to one another. The angular alignment of the ends of the connector body 12 results in a lower profile of the nutrition tubing in relation to the gastrostomy device 44, when the connector body 12 is inserted into the connector sleeve 22.

While the specific embodiments have been illustrated and described, numerous modifications come to mind without significantly departing from the spirit of the invention and the scope of protection is only limited by the scope of the accompanying claims.

I claim:

1. An apparatus for connecting medical tubing, which comprises:

a connector body having an inner surface which defines a passageway, and an outer surface having a recessed shoulder on at least a portion of its extent;

a connector sleeve having an inner surface which defines a passageway of slightly greater diameter than the outer surface of the connector body;

a latch on the inner surface of the connector sleeve extending radially inward in a protruding position, and a compressible support element located radially outward of the latch to bias the latch to said protruding position:

the latch being movable radially outward to compress the support element when subjected to a mechanical force by the outer surface of the connector body when the connector body is inserted into the connector sleeve; and, said latch is positioned to move into said protruding position and engage with the recessed shoulder of the connector body inserted within the connector sleeve;

said outer surface of the connector body having a void area on a portion without said recessed shoulder;

the void area having an outer surface radially outward from the recessed shoulder; and, whereby the outer surface of the void area may be aligned with the latch, such that the support element is compressed and the latch is positioned radially outward from said protruding position.

2. A locking union for connecting medical tubing, comprising:

a connector body attached to a first tube, the connector body having an inner lumen in fluid communication with an inner lumen of the first tube, and having an outer surface, at least a portion of the outer surface having an outer periphery and an outer diameter;

a recess in the outer surface of the connector body across at least a portion of the outer periphery to define a recess area;

a connector sleeve attached to an end of a second tube, the connector sleeve having a circular inner surface which defines a passageway of an inner diameter, the inner diameter is slightly greater than the outer diameter of the connector body such that at least a terminal portion of the connector body is insertable into the connector sleeve;

a latch on the inner surface of the connector sleeve extending radial inward into the passageway in a protruding position, the latch being in movable attachment and biased in the protruding position by a compressible support element located adjacent and radially outward the latch such that the latch is movable radially outward to a retracted position to compress the support element when subject to a mechanical force by the outer surface of the connector body when the connector body is inserted into the connector sleeve;

the latch being positioned to insert into the recess of the connector body by movement of the latch to the protruding position such that the connector body is locked in inserted position within the connector sleeve;

the recess of the connector body is a groove formed in the outer surface of the connector body across a portion of the outer periphery to define the recess area;

a void area across another portion of the outer periphery, the void area having an outer surface radially outward from said groove whereby the outer surface of the void area may be aligned with the latch, such that the support element is compressed and the latch is positioned radially outward from said protruding position.

3. A locking union for connecting medical tubing, comprising:

a connector body attached to a first tube, the connector body having an inner lumen in fluid communication with an inner lumen of the first tube, and having an outer surface, at least a portion of the outer surface having an outer periphery and an outer diameter;

a recess in the outer surface of the connector body across at least a portion of the outer periphery to define a recess area;

a connector sleeve attached to an end of a second tube, the connector sleeve having a circular inner surface which defines a passageway of an inner diameter, the inner diameter is slightly greater than the outer diameter of the connector body such that at least a terminal portion of the connector body is insertable into the connector sleeve;

a latch on the inner surface of the connector sleeve extending radial inward into the passageway in a protruding position, the latch being in movable attachment and biased in the protruding position by a support element located adjacent the latch such that the latch is movable radially outward to a retracted position when subject to a mechanical force by the outer surface of the connector body when the connector body is inserted into the connector sleeve;

the latch being positioned to insert into the recess of the connector body by movement of the latch to the protruding position such that the connector body is locked in inserted position within the connector sleeve;

the recess of the connector body is a groove formed in the outer surface of the connector body across a portion of the outer periphery to define the recess area;

a void area across another portion of the outer periphery, the void area having an outer surface radially outward from said groove whereby the outer surface of the void area may be aligned with the latch, such that the latch is positioned radially outward from said protruding position;

the support element includes an area radially outward of the latch which is constructed of a resilient elastic material; and, the latch is constructed of a rigid material relative to the elastic material and compresses the elastic material when the latch is forced into the retracted position.

4. The locking union of claim 3 wherein:

the latch is constructed from plastic; and, the resilient elastic material is constructed from silicone rubber.

5. A connector for two conduits, comprising:

a connector body having an inner lumen in fluid communication with an inner lumen of a first conduit, said connector body having an outer surface periphery with a recess across a portion of the outer periphery, and a void area across the remaining portion of the outer periphery with an outer surface radially outward from said groove;

a connector sleeve attached to a second conduit, said connector sleeve having an inner surface and suitable for receiving at least part of the connector body; and, a latch extending radially inward from the inner surface of the connector sleeve in a protruding position, and a means for supporting the latch in said protruding position by a compressible support element adjacent the latch, the latch being movable radially outward to a retracted position when subject to a mechanical movement by the outer surface of the connector body when the connector body is inserted into the connector sleeve, the latch being insertable into the recess of the connector body by movement of the latch to the protruding position when connector body is inserted within the connector sleeve such that the latch is aligned with the recess.

6. The connector according to claim 5 wherein said means for supporting the latch includes an outer body of resilient elastic material.

7. The connector according to claim 6 wherein the resilient elastic material includes silicone.

\* \* \* \* \*